United States Patent
Spaas et al.

(10) Patent No.: US 12,136,176 B2
(45) Date of Patent: *Nov. 5, 2024

(54) AUGMENTED REALITY HEADSET FOR MEDICAL IMAGING

(71) Applicant: ARSPECTRA SARL, Foetz (LU)

(72) Inventors: Cedric Spaas, Ghent (BE); Ricardo Polar, Esch-sur-Alzette (LU)

(73) Assignee: ARSPECTRA SARL, Foetz (LU)

( * ) Notice: Subject to any disclaimer, the term of this patent is extended or adjusted under 35 U.S.C. 154(b) by 0 days.

This patent is subject to a terminal disclaimer.

(21) Appl. No.: 17/774,444

(22) PCT Filed: Oct. 30, 2020

(86) PCT No.: PCT/EP2020/080578
§ 371 (c)(1),
(2) Date: May 4, 2022

(87) PCT Pub. No.: WO2021/089440
PCT Pub. Date: May 14, 2021

(65) Prior Publication Data
US 2022/0387130 A1    Dec. 8, 2022

(30) Foreign Application Priority Data

Nov. 5, 2019 (GB) .................................. 1916068

(51) Int. Cl.
*G06T 19/00* (2011.01)
*A61B 34/10* (2016.01)
(Continued)

(52) U.S. Cl.
CPC ............ *G06T 19/006* (2013.01); *A61B 34/10* (2016.02); *A61B 90/00* (2016.02); *A61B 90/36* (2016.02);
(Continued)

(58) Field of Classification Search
None
See application file for complete search history.

(56) References Cited

U.S. PATENT DOCUMENTS 10,616,568 B1    4/2020  Lin et al.
2009/0052623 A1  2/2009  Tome et al.
(Continued)

FOREIGN PATENT DOCUMENTS

JP    2017524281 A    8/2017
JP    2018514748 A    6/2018
(Continued)

OTHER PUBLICATIONS

Kink "International Search Report" for Application No. PCT/EP2020/080578; Jan. 2021; four pages.
(Continued)

*Primary Examiner* — Jwalant Amin
(74) *Attorney, Agent, or Firm* — Studebaker & Brackett PC

(57) ABSTRACT

An augmented reality, AR, system (100) for use in a medical procedure is disclosed. The AR system (100) comprises an AR headset (2), and a processor (12), The AR headset (2) comprises a camera (6a, 6b), a near eye display (4a, 4b) and a distance sensor (10a, 10b). The processor (12) is configured to adjust the position of the image obtained by the camera (6a, 6b) on the display (4a, 4b) throughout the medical procedure based on changes in the distance measured by the distance sensor (10a, 10b).

15 Claims, 10 Drawing Sheets

(51) Int. Cl.

| | |
|---|---|
| *A61B 90/00* | (2016.01) |
| *A61B 90/50* | (2016.01) |
| *G02B 27/00* | (2006.01) |
| *G02B 27/01* | (2006.01) |
| *G06F 3/01* | (2006.01) |
| *G06T 7/70* | (2017.01) |
| *G06T 19/20* | (2011.01) |
| *H04N 13/239* | (2018.01) |
| *H04N 13/271* | (2018.01) |

(52) U.S. Cl.
CPC ............ *A61B 90/361* (2016.02); *A61B 90/37* (2016.02); *A61B 90/39* (2016.02); *A61B 90/50* (2016.02); *G02B 27/0093* (2013.01); *G02B 27/0101* (2013.01); *G02B 27/017* (2013.01); *G02B 27/0172* (2013.01); *G02B 27/0179* (2013.01); *G06F 3/011* (2013.01); *G06F 3/013* (2013.01); *G06T 7/70* (2017.01); *G06T 19/20* (2013.01); *H04N 13/239* (2018.05); *H04N 13/271* (2018.05); *A61B 2034/105* (2016.02); *A61B 2034/107* (2016.02); *A61B 2090/365* (2016.02); *A61B 2090/371* (2016.02); *A61B 2090/372* (2016.02); *A61B 2090/3941* (2016.02); *A61B 2090/395* (2016.02); *A61B 2090/502* (2016.02); *A61B 2562/0257* (2013.01); *G02B 2027/0127* (2013.01); *G02B 2027/0134* (2013.01); *G02B 2027/0138* (2013.01); *G02B 2027/014* (2013.01); *G02B 2027/0187* (2013.01); *G06T 2210/41* (2013.01); *G06T 2219/2004* (2013.01)

(56) References Cited

U.S. PATENT DOCUMENTS

| | | |
|---|---|---|
| 2015/0085087 A1* | 3/2015 | Vienne ................ H04N 13/144 |
| | | 348/51 |
| 2019/0289284 A1 | 9/2019 | Smith et al. |
| 2019/0310705 A1 | 10/2019 | Hincapie Ramos |
| 2022/0391013 A1* | 12/2022 | Vlaskamp ................ G09G 5/38 |

FOREIGN PATENT DOCUMENTS

| | | |
|---|---|---|
| KR | 10-2018-0136219 A | 12/2018 |
| WO | 2015/179446 A1 | 11/2015 |
| WO | 2016/048911 A1 | 3/2016 |
| WO | 2016/090336 A1 | 6/2016 |
| WO | 2018/176015 A1 | 9/2018 |
| WO | 2020/023672 A1 | 1/2020 |

OTHER PUBLICATIONS

Kink "Written Opinion of the International Search Authority" for Application No. PCT/EP2020/080578; Jan. 2021; nine pages.

Mondal et al. "Optical see-through cancer vision goggles enable direct patient visualization and real-time fluorescence-guided oncologic surgery"; Annals of Surgical Oncology; Feb. 2017; 24(7): 1897-1903; doi: 10.1245/s10434-017-5804-8.

Zhu et al. "Compact wearable dual-mode imaging system for real-time fluorescence image-guided surgery"; Journal of Biomedical Optics; Sep. 2015; 20(9): 096010 (six pages); doi:10.1117/1.JBO.20.9.096010.

Office Action mailed by the Japan Patent Office on May 14, 2024, which corresponds to Japanese Patent Application No. 2022-526430 and is related to U.S. Appl. No. 17/774,444; with English translation.

* cited by examiner

←---→ SET USING CALIBRATION PROCEDURE
←-·-→ DYNAMIC CALCULATED SPATIAL RELATIONSHIP
←——→ REGISTERED OR KNOWN SPATIAL RELATIONSHIP

| | |
|---|---|
| ←---▶ | SET USING CALIBRATION PROCEDURE |
| ◀---▶ | DYNAMIC CALCULATED SPATIAL RELATIONSHIP |
| ◀──▶ | REGISTERED OR KNOWN SPATIAL RELATIONSHIP |

AUGMENTED REALITY HEADSET FOR MEDICAL IMAGING

FIELD

The present invention relates to augmented reality system for use in medical procedures.

BACKGROUND

Fluorescence-based intra-operative surgical guidance is becoming a widely used procedure. This growth is especially focused on clinical approaches with indocyanine green (ICG) as the fluorescent marker, detected in the near-infrared spectrum (NIR).

Several medical imaging devices have been commercialized to allow ICG-based guidance in surgery. The approach is used for blood flow assessment, vessel patency, perfusion evaluation (especially in reconstructive and bypass surgeries), lymphatic imaging, and surgical procedures as sentinel lymph node identification and mapping. Further research efforts target the potential for imaging molecular tracers that report on new vascular, structural, metabolic, immunologic, or genetic features of the tissue. The application rates and range of ICG in medical procedures are growing rapidly.

The process involves injecting the fluorophore just before the surgical procedure. Near-infrared light is then shone onto the target area exciting the molecular ligands, which in response emit light with a specific wavelength. A camera sensitive to this range of the light spectrum is then used to detect the light to form an image which clearly denotes the target tissues.

This approach allows to significantly improve the detection and removal of primary tumour nodules of various cancer types as well as lingering metastases in sentinel lymph nodes, for instance in lung cancer surgery. Other uses include use in breast cancer surgery with lumpectomy or mastectomy and planned auxiliary sentinel node biopsy procedures.

Current systems are based on a mobile camera unit that acquires the emitted light with the visualisation of the detected image on an external screen next to the operation table. During the procedure the surgeon has to remove their focus from the area of the patient on which they are operating and subjectively compare the displayed data taken from a different point of view, with their real world view of the patient's actual body. This continuous comparative action makes fluorescence imaging cumbersome and especially limits its ability to accurately map the fluorescence-labelled tissues displayed with what the surgeon can see. In this latter subjective step, despite excellent professional training, significant amounts of precision, completeness, concentration, and time-efficiency are lost.

It is desirable to have a way in which the detected view of the target tissue through fluorescence imaging can be more easily and accurately correlated with the surgeon's actual real world view of the patient. This could lead to the prospect of making the procedure quicker and less prone to human error.

SUMMARY OF INVENTION

According to an aspect, there is provided an augmented reality, AR, system for use in a medical procedure. The AR system comprises: an AR headset, and a processor. The AR headset comprises: a camera configured to detect light from a target; a near-eye display positioned between a wearer's eyes and the target, the display configured to display an image of the target based on the light detected by the camera, such that the image overlays a wearer's view of the target; and a distance sensor, configured to determine a distance between the headset and the target throughout a medical procedure. The processor is configured to: determine a mismatch between the image of the target obtained from the camera and the wearer's view of the target based on the value of the distance measured by the distance sensor, and a position of the wearer's eyes; adjust the position of the image on the display such that it is corrected based on the determined mismatch such that the image matches the wearer's view of the target; and repeat the determination of the mismatch and the adjustment of the position of the image throughout the medical procedure to take into account changes in the distance measured by the distance sensor throughout the medical procedure.

By displaying the image of the target in a display of an augmented reality device it provides the wearer performing the medical procedure with the view of the image generated by the light from the target in their direct line of sight. This removes the need for them to adjust their gaze to switch between viewing the image on an external display and their real world view of the patient.

The difference between the position of the wearer's eyes and the distance to the target enables the discrepancy between the views to be adjusted for. This is because the camera will not have the same view as the wearer's view of the target. This correction is performed throughout the procedure through the distance sensor measuring the distance between the headset and the target. This allows for a dynamic updating of the position of the augmented image on the display such that the image that is displayed is at the correct position such that it overlaps the wearer's real world view of the target. This ensures that the augmented image in the display matches the exact position on the target from which it was emitted in the wearer's view.

This can provide the medical professional wearing the headset with an accurate mapping between the augmented generated image and the actual patient. This can enable a much greater precision when carrying out a surgical procedure on the patient.

Preferably, the processor is further configured to determine the mismatch between the image of the target obtained from the camera and the wearer's view of the target by being configured to: assign a position in space to act as a fixed reference point; generate a 3D model of the target based on the light detected by the camera; determine the position and orientation of the target relative to the fixed reference point based on the distance measured by the distance sensor; determine the position of the wearer's eyes relative to the fixed reference point; determine the position and orientation of the headset relative to the fixed reference point.

By determining the position and orientation of the headset, and the target and the position of the wearer's eyes, with respect to a fixed reference point their position and orientation are transformed into a fixed reference frame with respect to one another. This allows the relative positioning of the image of the target on the display to be adjusted through the geometric relationships between the wearer's eyes and the headset with respect to the target through the continually updated measurement of the distance to the target. In addition to the position of the wearer's eyes the orientation of the wearer's eyes may also be determined.

The fixed reference point may be on the headset. For instance, it may be located at a point between where the wearer's eyes would be located. Alternatively, it may be set as the point where the camera, distance sensor or display is located on the headset. The fixed reference point need not be on the headset and may instead be a point that is external to the headset. The fixed reference point may be a position in 3D space represented in 3D coordinates. The position and orientation of the wearer's eyes, the target, and the headset may be converted to 3D coordinates.

The position and orientation of the headset relative to the fixed reference point may be the position and orientation of at least one of the display, distance sensor, and camera. The positioning of the display, camera and/or distance sensor relative to each other may be known. This allows the displacement between each of these to be taken into account when adjusting the position of the image. As their positions relative to each other may be static they may be known. The processor may receive these position values. For instance, they may be stored in memory. When the fixed reference point is a position on the headset the distance between the display, distance sensor and camera relative to the fixed reference point may be known from knowing the geometry of the headset.

Alternatively, if not already known the value of these positions and orientations may be measured through one or more sensors.

Preferably, the processor is further configured to adjust the position of the image on the display such that it is corrected based on the determined mismatch by being configured to: set the position of the 3D model of the target relative to the fixed reference point; render the 3D model of the target to form the adjusted image based on the determined positions and orientations of the target and headset and position of the wearer's eyes; and display the adjusted image on the display.

In this way, the generated 3D model of the target is within the same frame of reference as the headset and wearer's eyes. This enables rendering of the 3D model of the target such that the image displayed on the display takes into account the position of the headset, target and wearer's eyes.

Preferably, the processor is further configured to determine the disparity of the wearer's eyes. The disparity, or binocular disparity is the difference between the points of projection of the image in the wearer's two eyes. The disparity may be determined based on the determined distance to the target. It may be also determined based on the position of the wearer's eyes. This may be based on the interpupillary distance (IPD), and/or the distance between the headset and the wearer's eyes. Preferably, the processor is further configured to determine the mismatch between the image of the target obtained from the camera and the wearer's view of the target by being configured to: determine the disparity of the wearer's eyes from the determined distance and the position of the wearer's eyes.

The distance to the target is inversely proportional to disparity. By knowing the distance to the target and the position of the wearer's eyes it is possible to determine the disparity of each of the eyes. This enables the alignment of the generated image in the display to be updated such that it matches the wearer's view of the target for each of the wearer's eyes. The adjustment of the image in the display may be different for each of the wearer's eyes.

In some aspects the AR headset may further comprise an eye tracking sensor, the eye tracking sensor configured to continually determine the position of the wearer's eyes throughout the medical procedure, such that the repetition of the determination of the mismatch and the adjustment of the position of the image throughout the medical procedure takes into account changes in the position of the wearer's eyes throughout the medical procedure.

In this way, the position of the wearer's eyes throughout the medical procedure can be tracked and used to update the position of the generated image in the display. Throughout the medical procedure the position of the wearer's eyes will not be fixed with their view and gaze varying throughout the procedure. The accuracy of the positioning of the generated image over the wearer's view can be improved by the continual determination of the position of the wearer's eyes and their position relative to the target and the headset. The eye tracking sensor may be configured to also determine the orientation of the wearer's eyes throughout the medical procedure.

The eye tracking sensor may also determine the focus of the wearer's eyes, i.e. the position of where they are focusing on at any particular time. In this way the generated image can be displayed such that it is displayed in focus at all time in the wearer's view of the target.

The eye tracking sensors may be a plurality of eye tracking sensors. For instance, there may be a single sensor that tracks each eye. Alternatively, a single tracking sensor may track the position of both eyes.

The eye tracking sensors may be an IR light source that scans the position of each eye to determine its position. This may be in the form of an LED or laser. Alternatively, or in addition, the eye tracking sensor may be an electric potential eye tracking sensor. The electric potential eye tracking sensor uses electrodes placed around the eye to measure the movement of the eye.

The processor may receive the position of the wearer's eyes. Preferably, the processor is further configured to obtain the position of the wearer's eyes through obtaining the interpupillary distance of the wearer's eyes.

The interpupillary distance is the distance between the pupils of each of the wearer's eyes. Each user will have an interpupillary distance that is unique to them. By knowing the interpupillary distance it can be used to determine the relative position of the wearer's eyes relative to the headset and/or the fixed reference point. It can also be used to determine the disparity of the wearer's eyes. This can help position the generated image on the display at the correct position for each of the wearer's eyes overlaying each eye's view of the target.

The interpupillary distance may be obtained automatically by the processor. This may be through the use of eye tracking sensors. Alternatively, the wearer may manually provide the interpupillary distance to the processor. For instance, the wearer, or someone else, may have measured the interpupillary distance manually.

Alternatively, the position of the wearer's eyes may be determined by a means other than using the interpupillary distance.

As outlined above, the position of the wearer's eyes may be determined using the eye tracking sensor. This might be the position of the wearer's eyes with respect to a fixed reference point, such as a point on the headset. Alternatively, the position of the wearer's eyes relative to the fixed reference point may be determined through a calibration procedure. This may be performed before the medical procedure, or if it is determined during the medical procedure that a further calibration is necessary. This calibration may involve the wearer viewing an external marker. Adjustments can then be made until the position of the image of the marker is matched to the wearer's view of the marker. This may involve the wearer manually adjusting parameters of the image generation such that the image of the marker is moved to overlay their view of the marker. The marker may be any type of marker including a dot, or line, or a reference motif with a known shape. This calibration enables the processor to determine the position and/or orientation of the wearer's eyes relative to the fixed reference point.

Preferably, the camera may comprise the distance sensor. Alternatively, the camera and distance sensor may be separate sensors.

The distance sensor may be a time of flight distance sensor and/or the sensor may be a depth sensor. Alternatively, the distance sensor may be a simultaneous localization and mapping (SLAM) sensor, a vSLAM sensor, a dot-marker pattern sensor, or a sensor that uses the same principle as a Kinect device. The distance sensor may be a sensor with the sole purpose of determining distance. Alternatively, the distance sensor may be a camera that is configured to perform the role of a distance sensor. For instance, the camera and the distance sensor might be the same. In this way the camera acts both as the camera and the distance sensor. Alternatively, there may be a plurality of cameras that act as the distance sensor.

Preferably, the AR system further comprises a light source, the light source configured to emit light such that it is incident on the target and subsequently detected at the camera.

The light source may be configured to transmit light towards the target such that when subsequently detected by the camera it forms an image representative of the target or a portion thereof. The light source may be fluorescence light source. Alternatively, the light source may be such that the image is formed through reflection of the light from the target.

The AR headset may comprise the light source. Having the light source on the headset may enable the camera and the light source to be focused on the same area of the target. This ensures that the wearer has control over the illumination of the light on the target. Alternatively, the light source might be an external light source that is not located on the headset.

Preferably, the light is near infra-red light. The medical procedure may be a fluorescence based guidance procedure. Near infra-red light can be used for fluorescent based guidance procedures. The light source may be configured to emit within these bands. The wavelength of the NIR light may be in the order of 780 nm. This is the excitation range for ICG. However, other wavelengths of NIR may be used depending on the molecular marker being used.

Alternatively, the light may be visible light or infrared light.

The camera may be configured to detect NIR light. The camera may be configured to detect in the range of wavelengths that the molecular marker being used transmits within. In the case of ICG this may be a wavelength of 810 to 860 nm, which depends on the type of tissue. The camera may be configured to detect the same wavelength band of light as the light source.

The camera may detect the light continuously throughout the medical procedure. In other arrangements the camera may be arranged to acquire light at time periods that are spaced throughout the medical procedure. In this way, the generated image in the AR display can be updated through the procedure.

In other embodiments, the image detected by the camera may be captured once during the medical procedure. This image may then not be updated throughout the procedure, only its position on the near eye display to account for changes in the position of the headset. This may be the case where it not expected that the image of the target acquired by the camera will change.

The processor may be further configured to convert the light detected by the camera into an image that is visible to the user. When the light that is emitted from the target is in the IR or NIR band, the wearer's eyes would traditionally not be able to view the light. This may be the case when the light is excited through fluorescence from the target. By converting the light, and displaying the image on the near eye display, it can be displayed in a way that the wearer can visualise the light reflected from the target. This image enhances the view of the wearer providing information that they could not previously see in their line of sight.

The AR headset may comprise the processor. This removes the need for leads or physical connections that are required between an external processor and the headset.

Alternatively, the processor may not be located on the headset. This may reduce the weight of the headset. For instance, the processor may be located on a server or computing system external to the headset. The processor may be connected to the headset through a wired connection. Alternatively, the processor may be connected to the headset through a wireless connection, such as WiFi, Bluetooth connectivity, or other type of RF connections.

In some aspects the headset may comprise a plurality of cameras configured to detect the excited light. Having a plurality of cameras to detect the excited light may enable the image to be detected from two different viewpoints. This can enable improved generation of the model of the target. In addition, it can provide more accurate estimates of the position of the headset relative to the target.

The near eye display may be a single display. Alternatively, the near eye display may be two displays, one display for displaying an image for each eye. The near eye display may be a waveguide. Alternatively, the display might be a beam splitter display, or a laser reflection display. The display may utilise mirrors to project the image into the wearer's view. The display may be made of glass and/or plastic. In this way it is transparent. The near eye display may be alternatively a lens. Or the near eye display may be a beam that projects the image into the eyes of the wearer such that the image is displayed on the retina. In this way the near-eye display may be a virtual retinal display.

The display and/or camera may comprise one or more filters. The filters may be configured to improve the detection of the specific wavelengths of light from the target, while removing the other signals at undesired wavelengths. Alternatively, or in addition, the filters may be positioned in front of the light source.

According to a further aspect there is provided a method of adjusting the position of an image in an augmented reality, AR, system for use in a medical procedure, the AR system comprising a AR headset and a processor, the method comprising: detecting light excited from a target; determining a distance between the headset and the target throughout a medical procedure; displaying on a near-eye display positioned between a wearer's eyes and the target, an image of the target based on the detected light, such that the image overlays a wearer of the headset's view of the target through the steps of: determining a mismatch between the image of the target obtained from the camera and the wearer's view of the target based on the value of the determined distance, and a position of the wearer's eyes; and adjusting the position of the image on the display such that it is corrected based on the determined mismatch.

According to a further aspect there is provided a non-transitory computer readable medium, that when executed on a processor is configured to perform the above method.

DETAILED DESCRIPTION

Figure 1:
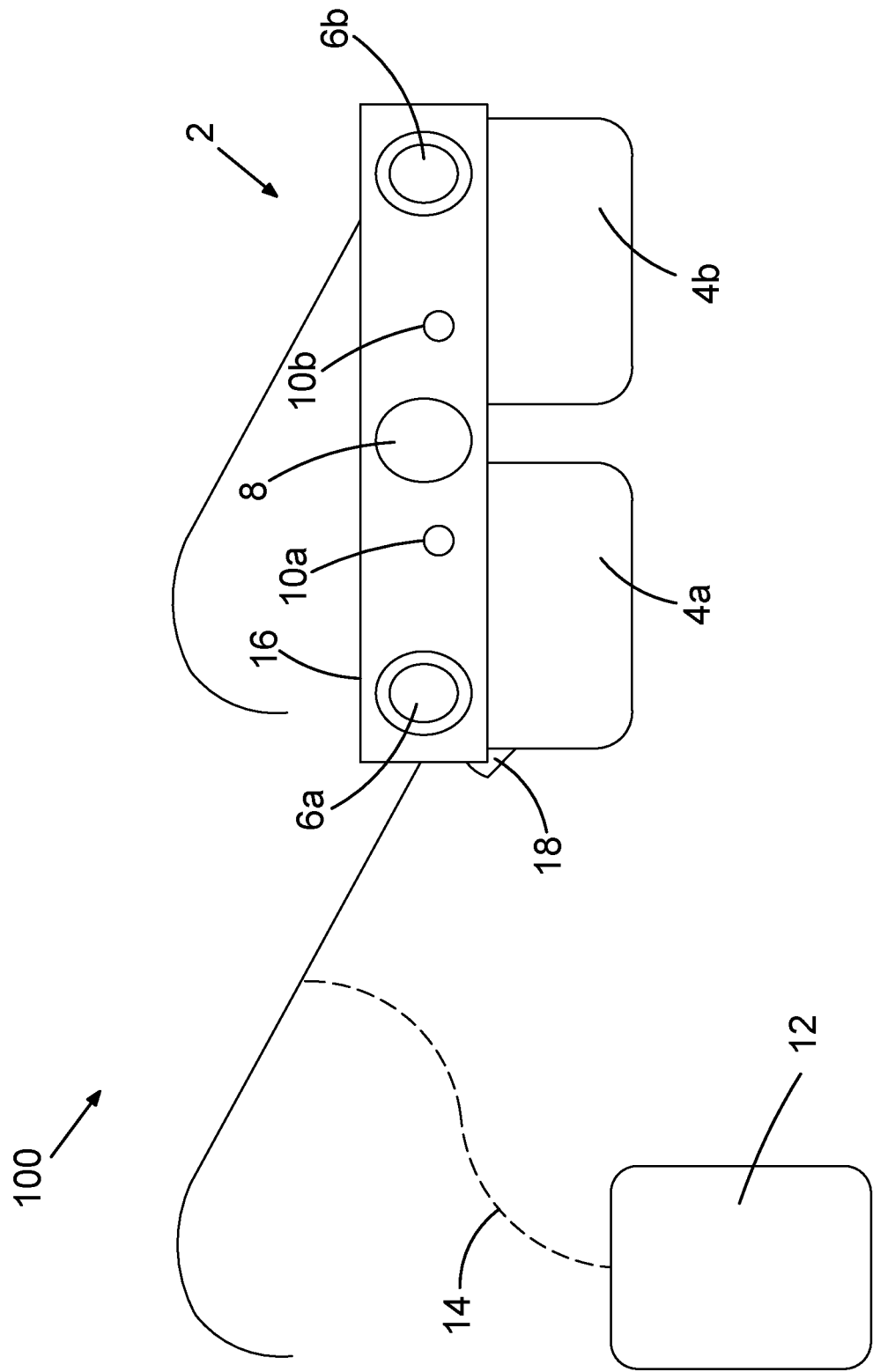
FIG. 1 shows an example augmented reality (AR) system according to the present invention.

FIG. 1 shows an augmented reality (AR) system 100 according to an embodiment of the present invention. The AR system 100 includes an AR headset 2 and a processor 12.

The augmented reality headset 2 has two displays a first display 4a and a second display 4b, the first display 4a for displaying an image to the right eye of the wearer of the headset and the second display 4b for displaying an image to the left eye of the wearer of the headset 2. The displays 4a and 4b are attached to a housing 16 of the headset 2.

Located on the housing 16 of the headset are two cameras 6a 6b. Camera 6a is located above the first display 4a, and camera 6b is located above the second display 4b. The cameras 6a 6b are capable of detecting near infrared (NIR) light.

Also located on the housing 16 is a light source 8. The light source 8 is NIR light source configured to emit NIR light. The light source 8 is located between the camera 6a and 6b, although it could be located at any position on the AR headset 2. Alternatively, the light source 8 may be located external to the AR headset 2.

Two distance sensors 10a and 10b are located on the housing 16 of the headset 2. The distance sensors are time of flight sensors configured to determine a distance to an object from the headset 2.

The headset 2 further includes an eye tracking sensor 18. The eye tracking sensor is located on the side of the headset that faces the head of the wearer.

The eye tracking sensor is configured to determine the position of the eyes of the wearer of the headset 2.

The processor 12 is located external to the AR headset 2. The processor may be a processor of a computer or other data processing device. The AR headset 2 is connected to the processor 12 through cable 14. The cable 14 is for sending signals between the headset and the processor 12. For instance, the data obtained from the cameras 6a 6b, eye tracking sensor 18, and distance sensors 10a 10b may be sent through cable 14 to the processor 12. The cable 14 also is for sending communication signals between the processor 12 and the headset 2 to control the camera 6a 6b, distance sensor 10a 10b, light source 8, and eye tracking sensor 18 to perform their functions.

FIGS. 2, 3, 5 and 7 show top down schematic views of the AR headset 2 according to the present invention, each Figure showing a headset 2 having a different arrangement of sensors to each other. The headset 2 is shown as being used in a fluorescence based guidance procedure.

The features of the AR headsets 2 illustrated in FIGS. 2, 3, 5 and 7 are illustrated with the same reference numerals to those illustrated in FIG. 1. The portion of the target 20, in this case the patient, from which the fluorescence image is being detected is also shown.

Figure 2:
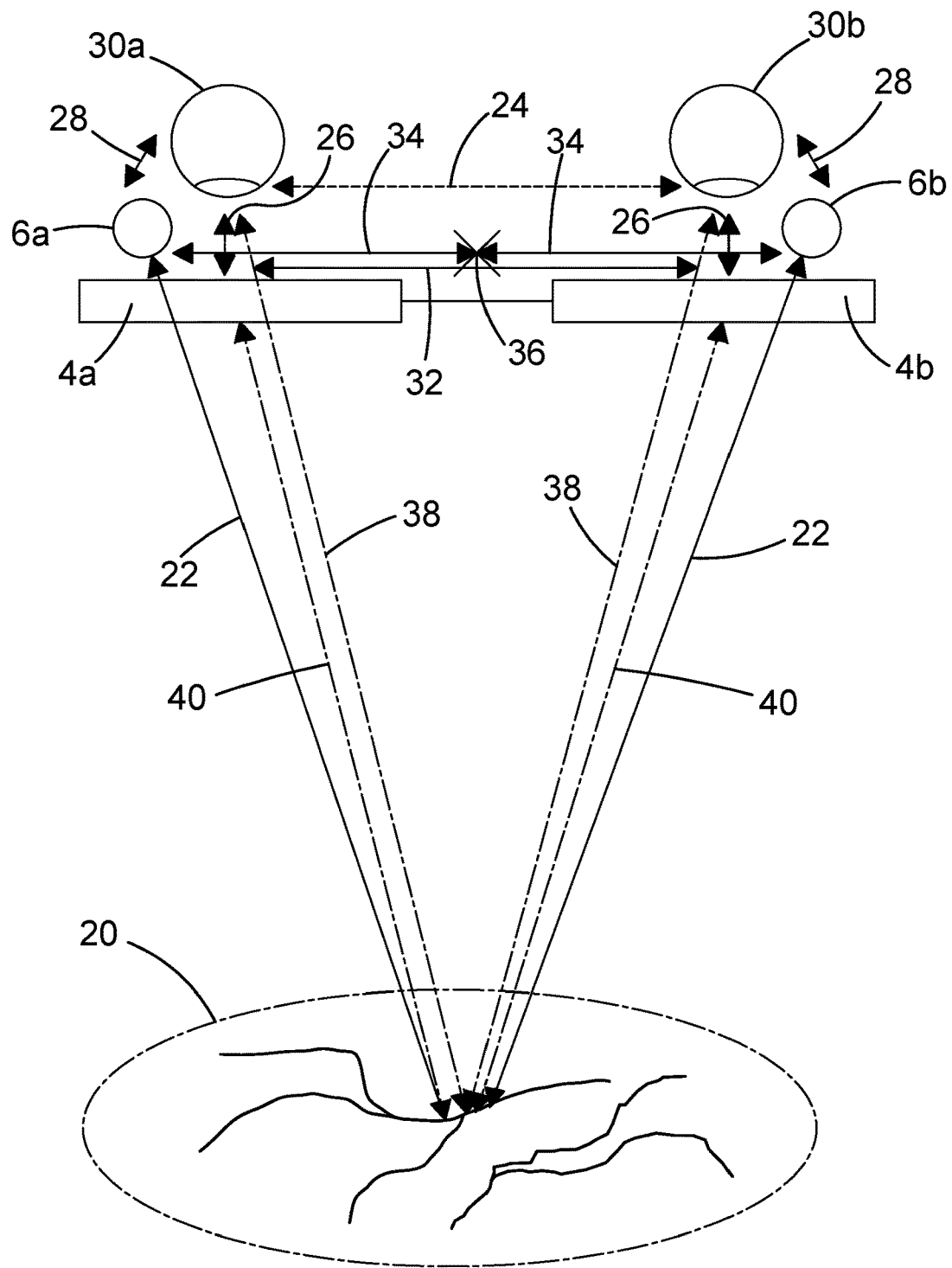
FIG. 2 shows a top down schematic view of an example AR system according to the present invention.

FIG. 2 shows an AR headset having two cameras 6a and 6b. The headset shown in FIG. 2 does not have a separate distance sensor. The two cameras 6a and 6b perform the role of the distance sensor, in addition to detecting the light from the target 20 to form the images.

Shown on FIG. 2 are the spatial relationships that are determined and used to adjust the position of the image that is generated in the display 4a 4b such that it matches the wearer's view of the target 20.

The distance 22 between the target 20 and each of the cameras 6a 6b is measured by the cameras 6a 6b.

As this AR headset 2 does not have eye tracking sensors, the distance 26 between each of the wearer's eyes and each of the displays 4a 4b is determined by a calibration procedure. The calibration procedure also involves the determination of the distance 28 between each of the cameras 6a and 6b and each of the wearer's eyes 30a 30b. The interpupillary distance (IPD) is also determined 24, this may also be through the calibration procedure. Alternatively the IPD may be known and input into the AR system by the wearer.

The distance 32 between the two displays 4a and 4b and the distance 34 between the two cameras 6a 6b is known from the geometry of the headset 2. This allows the determination of the distance 40 between the target 20 and the display and the distance 38 between the target and the wearer's eyes 30a 30b.

The determination of each of these distances allows them to be compared to the fixed reference point 36 on the headset 2. This enables the processor 12 to adjust the position of the image on the display such that the position of the image on the display for each of the eyes is matched to the wearer's view of the target.

Throughout the procedure the wearer may move their head relative to the patient 20. By continually measuring the distance 22 throughout the procedure the above calculation can be continually made to adjust the position of the image on the display throughout the procedure such that it matches the wearer's actual real-world view of the target.

Figure 3:
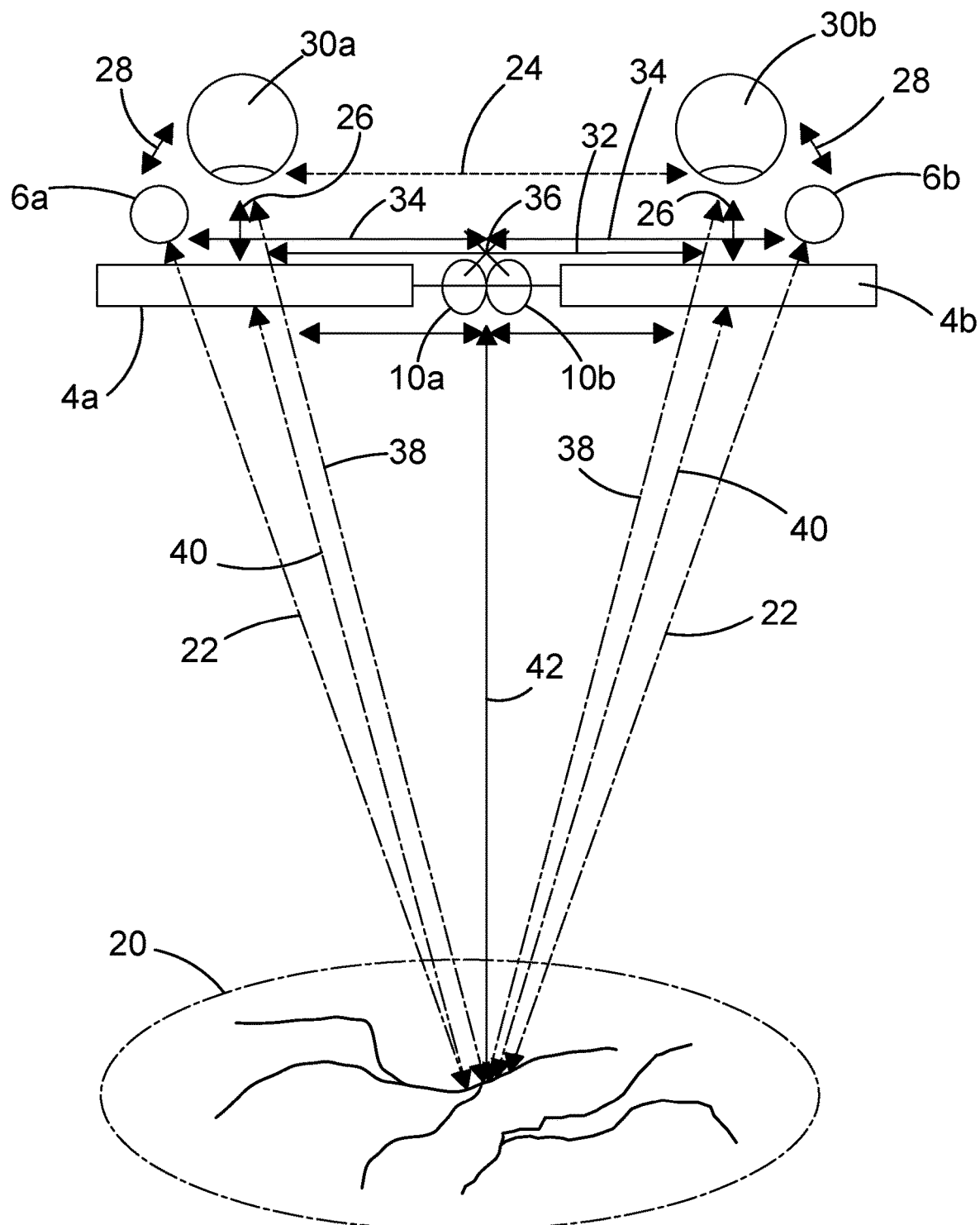
FIG. 3 shows a top down schematic view of a further example AR system according to the present invention.

FIG. 3 shows an AR headset having two cameras 6a and 6b and two distance sensors 10a and 10b. In this case the cameras 6a 6b perform the role of capturing the light emitted from the target 20 to form the image in the display 4a 4b. The distance sensors 10a 10b have the role of determining the distance between the patient 20 and the headset 2. The distance acquired by the distance sensors 10a 10b is shown as 42 in FIG. 3. The distance 22 between the target 20 and the cameras 6a 6b can be calculated from the determined distance value 42 and the known spatial relationships. The other spatial relationships shown in FIG. 3 with like reference numerals to those shown in FIG. 2 are determined in the same manner as described in relation to FIG. 2.

Figure 4:
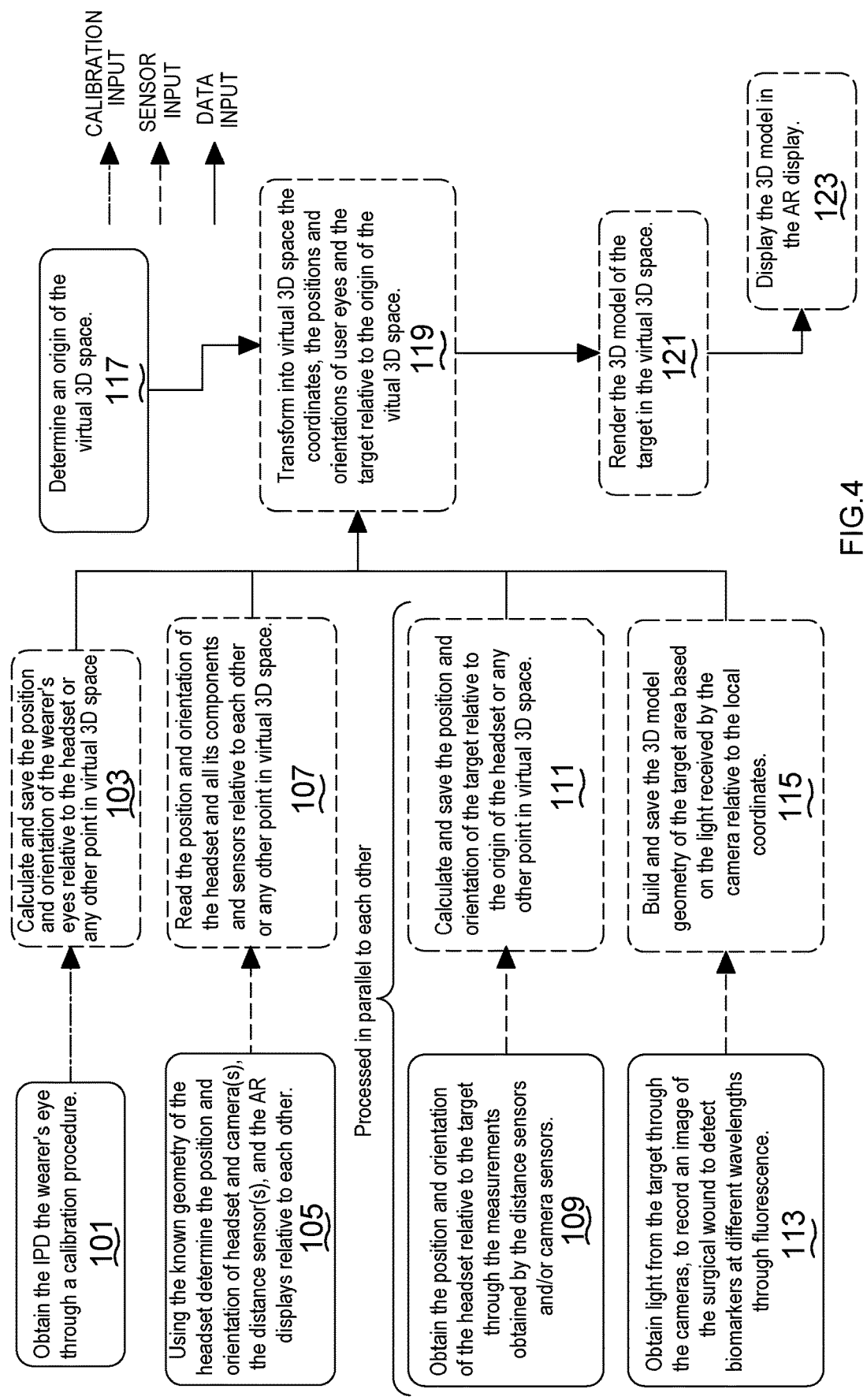
FIG. 4 shows a flow chart of steps performed in displaying a 3D image of a target using an example AR headset as shown in FIG. 2 or 3.

The steps performed by the AR system 100 of FIGS. 2 and 3 in displaying the image of the target are shown in FIG. 4.

At step 101 the IPD of the wearer's eyes is obtained through a calibration procedure. At step 103 the position and orientation of the wearer's eyes relative to the headset or any other point in virtual 3D space is calculated and saved.

At step 105 using the known geometry of the headset the position and orientation of headset and the camera(s), the distance sensor(s), the eye tracking sensors, and the AR/MR displays relative to each other is determined. This is based on the known geometries as shown in FIGS. 2 and 3. This enables at step 107 for the position and orientation of the headset and all its components and sensors relative to each other or any other point in virtual 3D space to be determined.

Steps 101 to 107 are carried out at the beginning of the medical procedure once the wearer has placed the AR headset on their head. It is taken that these determined values and spatial relationships do not change throughout the medical procedure, such that it is not further necessary to calculate these values throughout the procedure.

Step 109 involves obtaining the position and orientation of the headset relative to the target through the measurements obtained by the distance sensors (as in FIG. 3) and/or camera sensors (as in FIG. 2). The distance sensors may use time of flight, or any known type of measurement used to determine distance. The cameras 6a 6b may use vSLAM or any known method for determining distance through image sensors. At step 111 the position and orientation of the target relative to the origin of the headset or any other point in virtual 3D space are calculated and saved.

Step 113 involves obtaining light from the target through the cameras, to record an image of the surgical wound to detect biomarkers at different wavelengths through fluorescence. At step 115 the 3D model geometry of the target area can be built and saved based on the light received by the camera relative to the local coordinates. The local coordinates may be the same point on the headset or point in virtual space that the other positions and orientations are determined from.

The creation of the 3D model from images obtained by the camera may be carried out using photogrammetry. This involves the reconstruction in 3D of a subject from 2D captures using computer vision and computational geometry algorithms.

At step 117 the origin of the virtual 3D space is determined. As shown in FIGS. 2 and 3 this is the point 36 on the headset positioned between the two displays 4a and 4b. This virtual 3D space can be the same point by which the position and orientation of the headset, wearer's eyes and the 3D model are determined with respect to in steps 103, 107, 111, 115. This results in step 119 where the position and orientations of the wearer's eyes, and the target are transformed into virtual 3D space relative to the origin of the virtual 3D space.

At step 121 the 3D model of the target in virtual 3D space is then rendered.

At step 123 the rendered 3D model is then displayed in the display 4a 4b of the AR headset 2. This enables the 3D model of the target to be displayed automatically with the perspective view for each eye of the wearer.

Steps 109, 111 are performed throughout the medical procedure. This may be continually or at fixed points in time. This is because the wearer's head, and hence the AR headset 2 may move throughout the procedure. This will lead to the value determined in step 109 changing throughout the procedure.

Step 113 and 115 may also be performed throughout the medical procedure. This may be continually or at fixed points in time. This is due to the fact that the light detected by the camera may change throughout the procedure, as the medical procedure progresses. Steps 109, 111, and 113 and 115 may be run in parallel throughout the medical procedure.

As a result of this, steps 119, 121 and 123 may also be carried out throughout the medical procedure to take into account the updated data obtained from steps 109 to 115.

Figure 5:
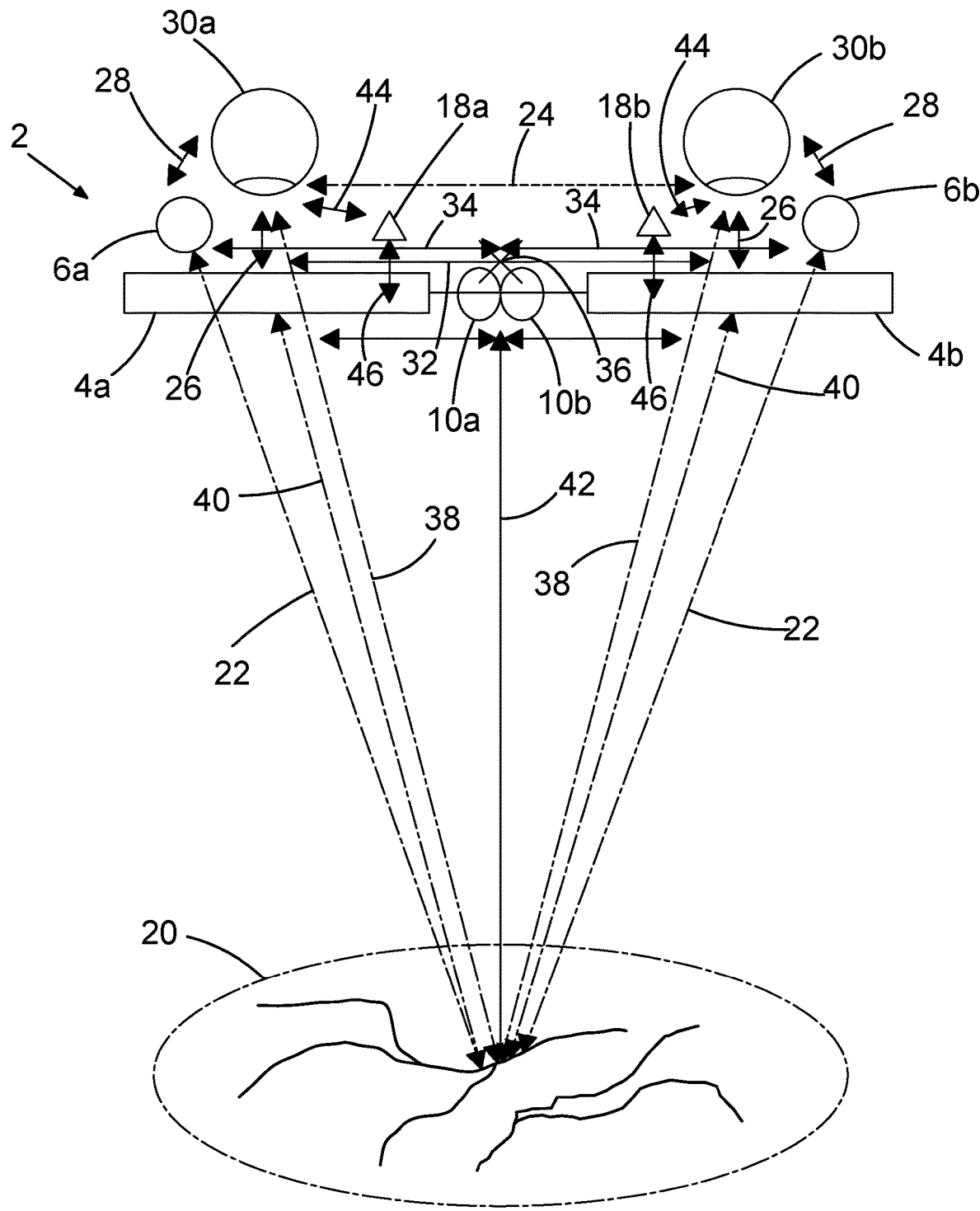
FIG. 5 shows a top down schematic view of a further example AR system according to the present invention.

FIG. 5 shows an AR headset 2 the same as FIG. 3, but also having two eye tracking sensors 18a and 18b. The same spatial relationships are shown in FIG. 5 as shown in FIG. 3. However, the distance 44 between the eye tracking sensors 18a 18b and the wearer's eyes 30a 30b are measured using the eye tracking sensors 18a 18b. This enables an accurate position and orientation of the wearer's eyes to be determined throughout the medical procedure. The distance 46 between the eye tracking sensors and the display is also determined. This may be either determined using the eye tracking sensors 18a 18b or may be a known spatial relationship based on the geometry of the headset.

The determination of the distance 44 and tracking of the wearer's eyes can be performed throughout the medical procedure. This enables the image of the target in the display to be updated to take into account the movement of the wearer's eyes. This can provide a more accurate matching of the wearer's view of the target to the image displayed on the AR display as the position of the wearer's eyes may be known throughout the procedure. The eye tracking sensor may determine the position of the wearer's eyes continually throughout the medical procedure or at fixed intervals in time. The eye tracking sensor may determine the position of the wearer's eyes at the same time as when the distance to the target is measured. This might be every 0.5 s. Alternatively, it may be more frequent than every 0.5 s. Alternatively it may be every 1 s. Use of the eye tracking sensors can provide a higher level of precision than without eye tracking sensors, this may allow sub-cm precision to be achieved as it takes into account changes in the wearer's eye movement. This is compared to the headset in FIGS. 2 and 3 where cm level precision can be obtained. In addition, if the position of the headset moves on the wearer's head the eye tracking sensors can correct for this movement performing a recalibration. In this way, having eye tracking sensors removes the need for an initial calibration to be performed such as through using a calibration reference at the beginning of the procedure.

The eye tracking sensor may be use near-infrared technology along with a camera (or other type of optical sensor) to track direction of the gaze of the wearer's eyes. This may involve using Pupil Center Corneal Reflection (PCCR). Alternatively, the eye tracking sensor may utilize electrooculography technology. This involves dry electrodes measuring the electrical potential of the skin around the eyes. Miniaturized electronics interpret electrical signals to calculate the eye movements. The sample rate may be around 256 samples per second, although this will depend on the type of camera. Alternatively, any type of eye tracking technology that is known may be used.

Figure 6:
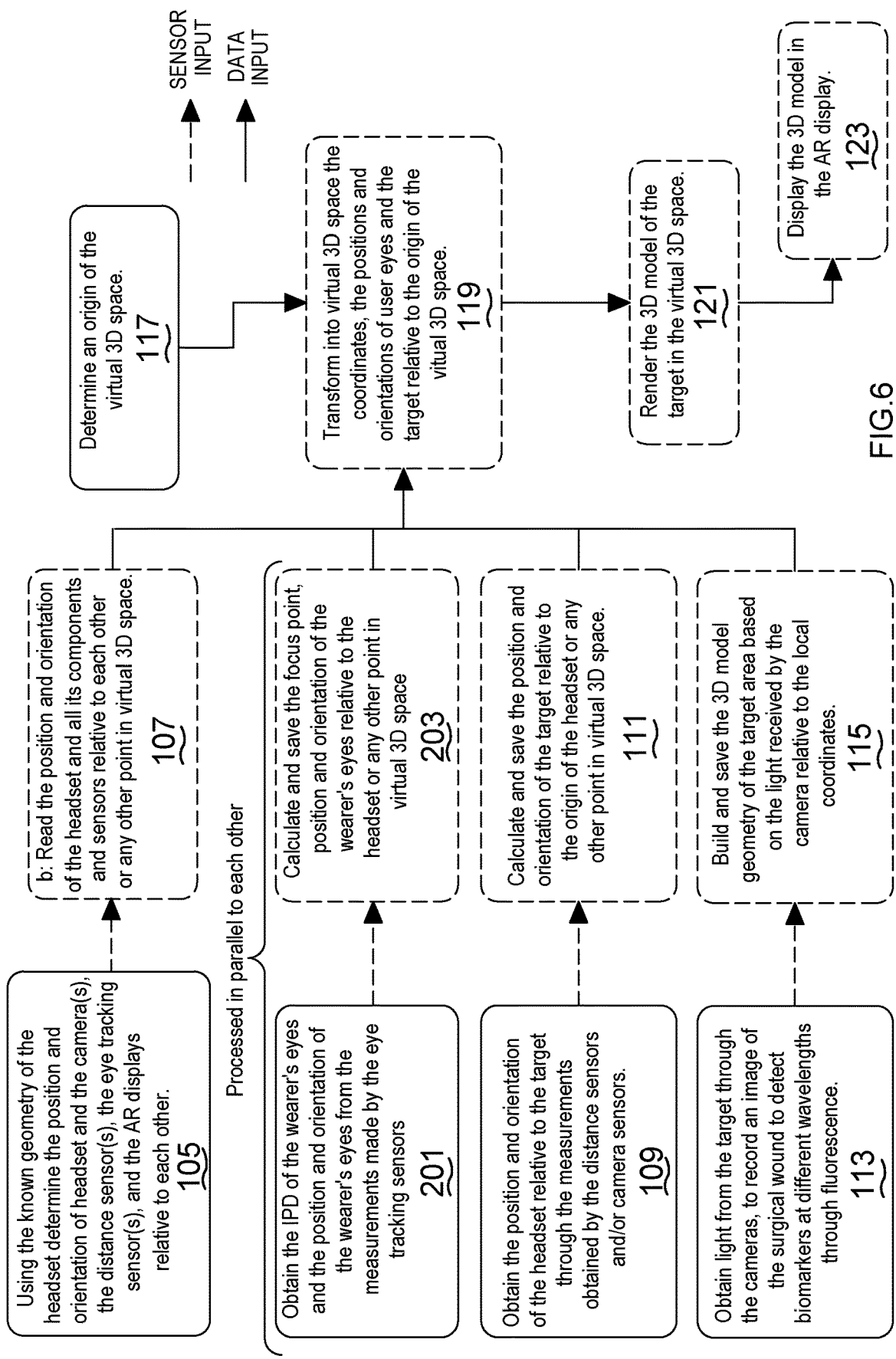
FIG. 6 shows a flow chart of steps performed in displaying a 3D image of a target using an example AR headset as shown in FIG. 5.

The steps performed by the AR system 100 of FIG. 5 in displaying the image of the target are shown in FIG. 6. Each of the steps in FIG. 6 that are identical to the steps in FIG. 4 is denoted by the same reference numeral.

Steps 201 and 203 in FIG. 6 are different to steps 101 and 103 in FIG. 4. Step 201 involves obtaining the IPD of the wearer's eyes, and the position and orientation of the wearer's eyes from the measurements made by the eye tracking sensors. Step 203 then involves calculating and saving the focus point, position and orientation of the wearer's eyes relative to the headset or any other point in virtual 3D space. This is based on the measurements made by the eye tracking sensors 18a 18b.

Steps 201 and 203 are carried out throughout the medical procedure as outlined above. This is then fed into step 119 to render and display the corrected image in steps 121 and 123.

Figure 7:
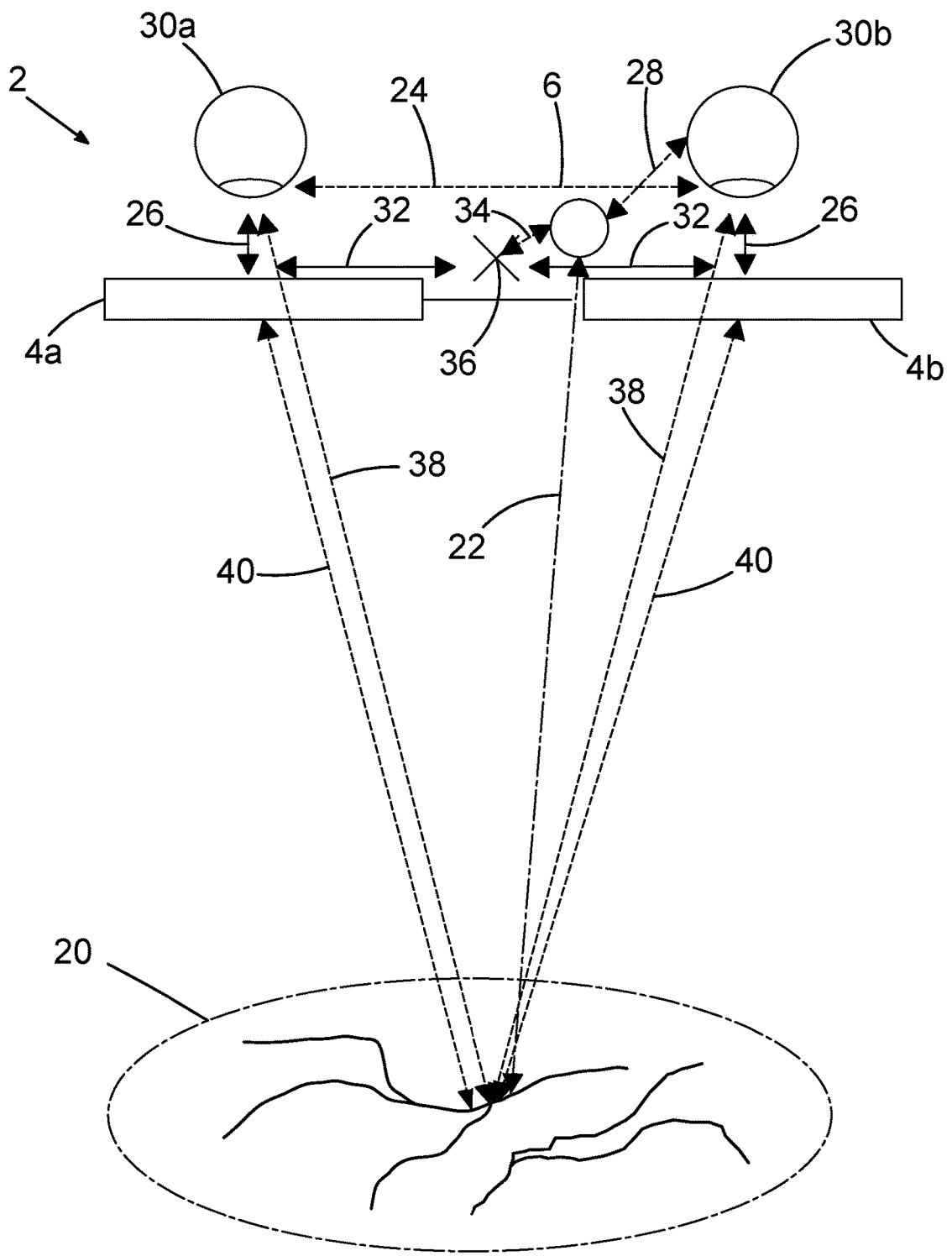
FIG. 7 shows a top down schematic view of a further example AR system according to the present invention.

FIG. 7 shows an AR headset 2 without a distance sensor or eye tracking sensors. The AR headset 2 of FIG. 7 is an AR headset 2 having only a single camera 6. Use of this AR headset requires additional computations to be performed initially to obtain the 3D representation and position of the target. This requires the wearer to move with respect to the target from multiple viewing angles at the beginning of the medical procedure such that the camera can obtain multiple images of the target to reconstruct a 3D model of the target. As the single camera 6 is the only sensor this cannot be done in real time throughout the medical procedure.

As can be seen from FIG. 7, the distance from the target to the display 40 and the user's eyes 38 is determined through the calibration, as is the distance 34 between the camera and the fixed reference point 36, unlike in FIG. 2. This is in addition to the IPD 24, the distance 28 between the camera and the wearer's eye, and the distance 26 between the wearer's eye and the display, as in FIG. 2. The distance 32 between the display and the fixed reference point 36 is known from the geometry of the headset.

Figure 8:
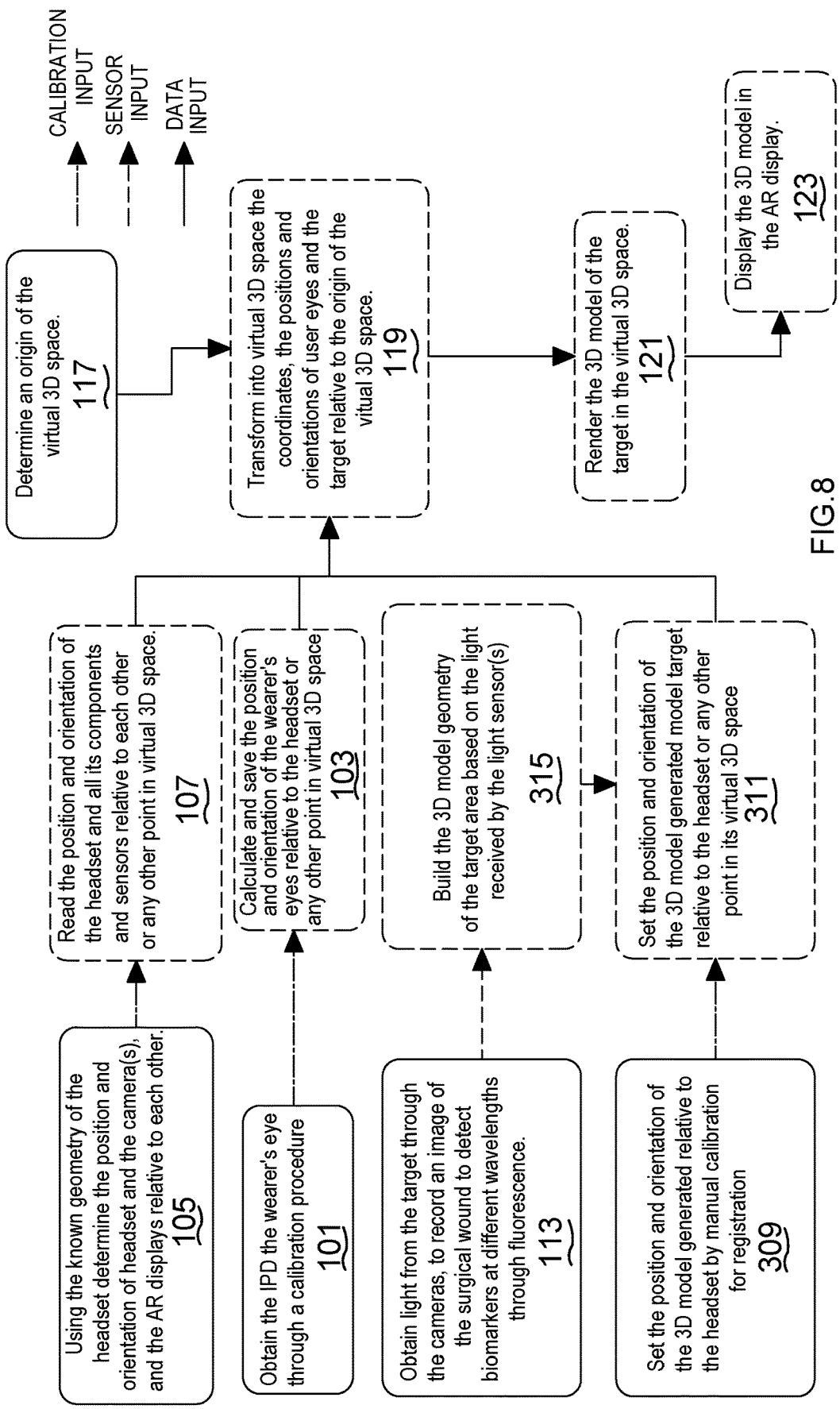
FIG. 8 shows a flow chart of steps performed in displaying a 3D image of a target using an example AR headset as shown in FIG. 7.

The steps performed by the AR system 100 of FIG. 7 in displaying the image of the target are shown in FIG. 8. Each of the steps in FIG. 8 that are identical to the steps in FIG. 4 is denoted by the same reference numeral.

As in FIG. 4 the position and orientation of the headset and the components of the headset are determined relative to the headset or a position in 3D space in step 107. The position and orientation of the wearer's eyes is also determined in step 103.

At step 315 a 3D model of the target area based on the light received by the camera 6 is generated. As there is only one camera, images are acquired at multiple different angles to form the 3D model through photometry algorithms. Therefore, using the AR headset of FIG. 7 having a single camera, it is not possible to generate the 3D model in real time, it must be done through an initial procedure using the photometry algorithms to scan the target and generate the 3D model. The position and orientation of the 3D model is set relative to the headset through the manual calibration 309. The wearer views the target scanning the surface. This enables the position and orientation of the 3D generated model of the target to be set relative to the headset or any other point in its virtual 3D space 311. The image of the 3D model is then transformed 119, rendered 121 and displayed 123 in the display as described in relation to FIG. 4.

Figure 9:
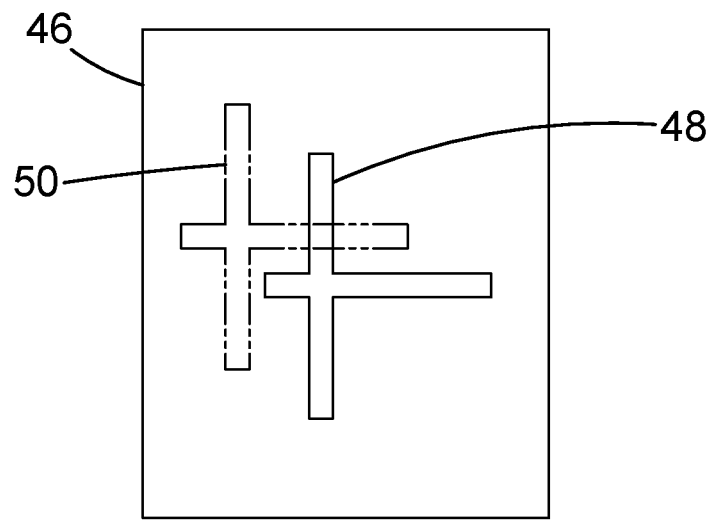
FIG. 9 shows a reference for a calibration procedure for use in displaying a 3D image of a target using an example AR headset.

As described above when the AR headset 2 does not have an eye tracking sensor to determine the position of the wearer's eyes, such as the headsets shown in FIGS. 2, 3 and 7, it is necessary to carry out a calibration procedure. This may involve the wearer viewing an external calibration reference 46 as shown in FIG. 9. The calibration reference in FIG. 9 is a reference motif 48. The actual position of the reference motif 48 is shown in FIG. 9. The uncorrected image of the reference motif is also shown denoted by 50. Adjustments are then made until the position of the image of the reference motif 50 is matched to the wearer's view of the reference motif 48. This may involve the wearer manually adjusting parameters of the image generation such that the image of the reference motif 50 is moved to overlay their view of the reference motif 48. This calibration enables the processor to determine the position of the wearer's eyes relative to the fixed reference point, such as a point on the headset.

Further details on how the alignment of the image on the display is corrected will now be described. This is one such example of how this may be achieved and alternative algorithms and methods may instead be applied.

To correct the image on the display based on the wearer's perspective view the camera's parameters including position and orientation and its optical properties are determined. Also determined to correct the image, are the 3D information of the target, and the disparity between the images displayed for each eye. The camera's position and orientation is determined based on steps 109 and 111.

The 3D information of the target is determined based on steps 113 and 115. The disparity between the images displayed for each eye is detailed based on steps 101, 103, 201, 203, 105, 107, 109 and 111.

The camera's parameters are determined based on intrinsic parameters representing the optical properties of the camera, and extrinsic parameters representing the position and orientation of the camera.

The intrinsic parameters represent the optical properties and can be estimated using the pinhole camera model. These include, the focal length of the camera, the aspect ratio of the plane where the camera's view is projected (i.e. the display), and the location of the image center (its principal point) where the optical axis intercepts the image plane.

The intrinsic properties of the pinhole camera model defines the projection transformation from the 3D space to 2D coordinate space of the display:

$$K = \begin{bmatrix} f_u & 0 & c_u \\ 0 & f_v & c_v \\ 0 & 0 & 1 \end{bmatrix}$$

Where f is the focal length from the center of the camera and perpendicular to the display and $c_{u,v}$ are the coordinates of the center of the display plane.

The position and orientation of the camera is determined by calculating its pose. This may be calculated using the sensors on the camera, for instance the distance sensor. The pose is represented by:

$$T_{pose} = \begin{pmatrix} R & T \\ 0 & 1 \end{pmatrix}$$

Where R is a 3×3 rotation matrix that represents the orientation of the camera, and T is a translation vector that represents the translation of the camera.

Based on the intrinsic and extrinsic parameters of the pinhole camera model, the 3D points can be mapped into the 2D image coordinates. This is shown by the matrix transformation below $T_{cam}$:

$T_{cam} = K * T_{pose}$

This is a multiplication of the camera pose (i.e. extrinsic parameters) and the projection matrix (i.e. the intrinsic parameters).

In the physical implementation, the pinhole camera model is not always precise because the different possible positions of the user's eyes relative to the display in runtime. Therefore, the following initial calibration is needed. Assuming that we know the translation vector $t_{eye}=[x, y, z]^t$ of the position of the eye with respect to the display, we can define the intrinsic matrix as follows for each eye:

$$K = \begin{bmatrix} f_u & 0 & 0 \\ 0 & f_v & 0 \\ 0 & 0 & 1 \end{bmatrix} \begin{bmatrix} z & 0 & -x \\ 0 & z & -y \\ 0 & 0 & 1 \end{bmatrix}$$

The vector $t_{eye}$ is dependent on the current position of the user's eyes with respect to the display, thus the parameters of the intrinsic matrix will change when the headset is repositioned on the user's head or when another user is wearing the headset and need re-calibration. If this is the case, the old matrix $K_0$ based on an old eye position $t_0=[x_0, y_0, z_0]^t$ could be updated to the new intrinsic matrix $K_1$.

$$K1 = K0 \begin{bmatrix} 1 + \Delta z/z0 & 0 & -\Delta x/z0 \\ 0 & 1 + \Delta z/z0 & -\Delta y/z0 \\ 0 & 0 & 1 \end{bmatrix}$$

The initial intrinsic and extrinsic matrix should be estimated for a specific headset and user configuration at run time in the calibration. There are different calibration procedures that use manual interactions to collect 3D and 2D correspondences by manually aligning a world reference point to 2D points displayed on the screen. For example, Tuceryan and Navad[a] introduced SPAAM (Single Point Active Alignment Method). They propose collecting individual 2D-3D point correspondences one at the time and then solving for all projection parameters at the same time. To do so, the user must align a 2D symbol (circle or cross) with a 3D object. The headset and 3D object are spatially tracked. Once we have at least 6 correspondences, they are used to create and solve a system of linear equation as an initial estimate of the parameters of the matrix K. Tracking the eyes position, these values can instead be computed automatically in runtime.

[a] Tuceryan, Mihran & Navab, Nassir. (2000). Single point active alignment method (SPAAM) for optical see-through HMD calibration for AR. 149-158. 10.1109/ISAR.2000.880938.

Figure 10:
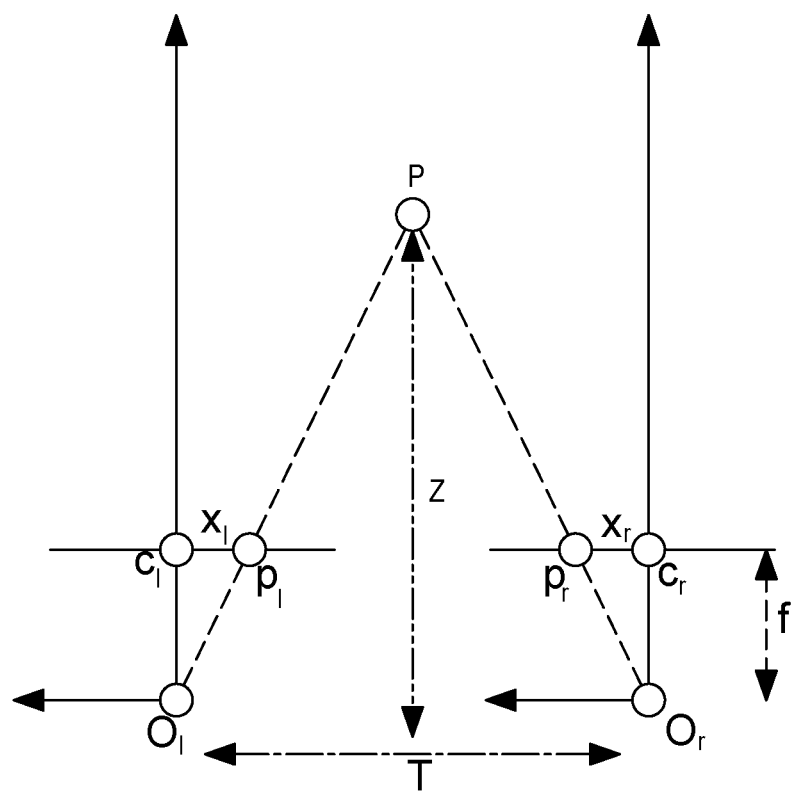
FIG. 10 shows a geometric relationship between a headset according to the present invention and the target for calculating disparity.

We will now describe how the disparity of each of the wearer's eyes may be calculated. This is then used to adjust the position of the image in the display. The calculation of disparity can be seen in FIG. 10, with the following terms in FIG. 10 defined as:

$O_l$=position of left eye
$O_r$=position of left eye
P=position of target
f=distance between eye and display
$p_l$ and $p_r$=principal point for left and right eye
$c_l$ and $c_r$=centre of the display for left and right eye
T=IPD
$x_l$ and $x_r$=difference between position of p and c for each eye
Z=distance to target From FIG. 10 it can be seen that the disparity $d=x_l-x_r$:

$$d = f\frac{T}{Z}$$

Thus, the disparity is inversely proportional to the distance to the target. By knowing the distance to the target throughout the medical procedure and the position of the wearer's eyes it is possible to update the alignment of generated 3D model of the target (the image) such that it is at the correct alignment for both of the wearer's eyes. This is further based on the estimated camera parameters as described above.

Figure 11:
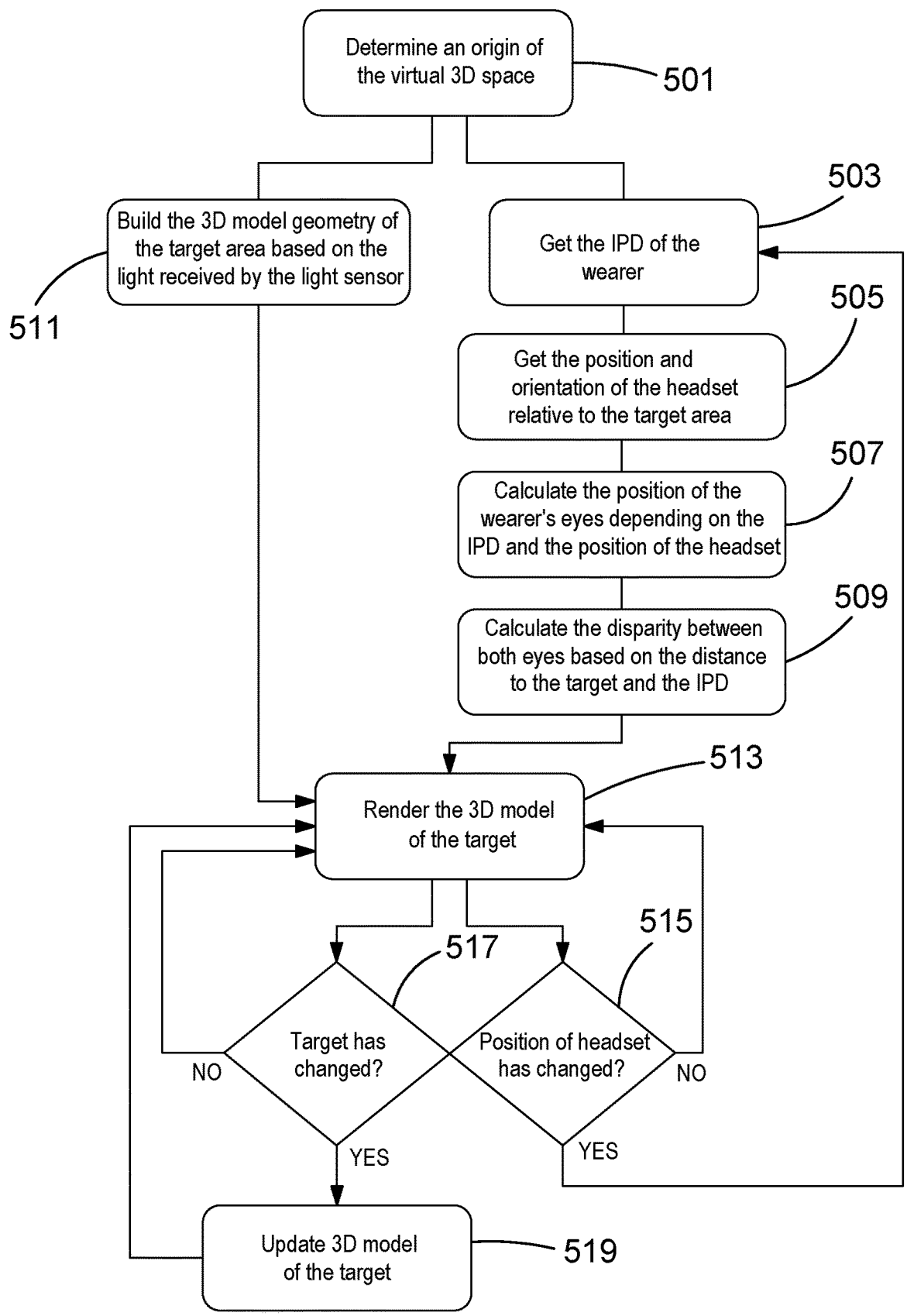
FIG. 11 shows a further flow chart of steps performed in displaying a 3D image of a target using an example AR headset as shown in FIG. 2, 3 or 5.

FIG. 11 shows a further flow chart of the method of adjusting the position of the image in the display for the headset of FIG. 2, 3 or FIG. 5.

At step 501 the origin in the 3D virtual space is determined. This is set to be a position from which the spatial relationships are determined.

At step 503 the IPD of the wearer is determined. This might be manually inputted, such as being entered by the wearer. Alternatively, where the headset has eye tracking sensors this may be determined through the eye tracking sensors.

At step 505 the position and orientation of the headset relative to the target is determined. This can be through receiving light from the target through the camera and analysing this light as explained above.

At step 507 the position of the wearer's eyes is determined based on the IPD and the position of the headset. This might be determined using a calibration procedure before the medical procedure. Alternatively, it might be through using the eye tracking sensors to determine the distance between the wearer's eyes and the headset.

At step 509 the disparity between both eyes is determined based on the distance to the target and the IPD. The distance to the target is determined through the distance sensor and/or camera.

At step 511 a 3D model geometry of the target is built based on the light received at the camera. Step 511 can be carried out in parallel whilst steps 503 to 509 are being performed.

Step 513 involves rendering the 3D model of the target. This is based on the 3D model built in step 511 and it is rendered based on the calculated disparity in step 509, and the position the headset relative to the target area as in step 505.

At step 515 a determination is made whether the position of the headset has changed. If it has steps 503 to 513 are then repeated. If it has not the same 3D model is rendered based on the previous calculated values.

At step 517 it is determined if the target has changed. If it has step 519 is performed to update the 3D model of the target with the updated 3D model rendered in step 513.

Having described aspects of the disclosure in detail, it will be apparent that modifications and variations are possible without departing from the scope of aspects of the disclosure as defined in the appended claims. As various changes could be made in the above constructions, products, and methods without departing from the scope of aspects of the disclosure, it is intended that all matter contained in the above description and shown in the accompanying drawings shall be interpreted as illustrative and not in a limiting sense.

Although FIGS. 2, 3, 5 and 7 show the spatial relationships that are determined, calculated or known, any other type of spatial relationships may be determined according to the present invention. All that is required is that the relationships between the headset, wearer and target can be determined such that the position on the image in the display can be corrected based on the view of each of the wearer's eyes.

It is described above that the creation of the 3D model from images obtained by the camera may be carried out using photogrammetry. Alternatively, triangulation methods may be used. This may include laser triangulation. This involves the projection of a laser beam onto the surface of the target. The measure of the deformation of the laser ray provides details of the geometry of the target. Alternatively, it may involve using the time of flight of a laser beam. The laser beam is projected onto the surface of the target and then collected by a sensor. The time of travel of the laser between its emission and reception gives the surface's geometrical information. These methods may involve the headset having one or more laser sources that can be used to perform these techniques. Any of the AR headsets shown in the figures may have such a laser source.

Although, it is shown that the eye tracking sensors are used in combination with distance sensor and cameras, the eye tracking sensors could be applied to any of the AR headsets described. For instance, the eye tracking sensors may be applied to an AR headset having only a single camera and no distance sensor.

Alternatively, the eye tracking sensors may be applied to a AR headset having a plurality of cameras and no distance sensor.

The detection of the image and associated actions are described as being performed by a camera. However, any type of image sensor/image sensing device may be used. The camera may be configured to detected still images or videos.

The AR headset is shown in the Figures as having two displays attached to a housing with two arms (temples). However, it will be understood that the AR headset of the present invention is not limited to such an arrangement, and any convention means of attaching a head mounted display (HMD) to a wearer could be envisaged. This may include using straps that pass around and/or over the head to hold the headset in place. Alternatively, an attachment means that attaches the device over the whole of the top of the head, such as a hat may be used.

The device is discussed in relation to being used during a florescence based guidance medical procedure. However, it may be used in any type of medical procedure where the aim is to detect radiation from the body or tissue of a patient to generate an image. It may also be used outside of medical procedures. For instance, it might find use in other industries where it is necessary to correct the position of an AR image on a display such that it matches the wearer's view. Such an industry may be architecture or construction.

The processor may be a processor for executing instructions in a data processing device. Instructions may be stored in a memory, for example. Processor may include one or more processing units (e.g., in a multi-core configuration) for executing instructions. The instructions may be executed within a variety of different operating systems on the data processing device, such as UNIX, LINUX, Microsoft Windows®, etc. More specifically, the instructions may cause various data manipulations on data stored in memory (e.g., create, read, update, and delete procedures). It should also be appreciated that upon initiation of a computer-implemented method, various instructions may be executed during initialization. Some operations may be required in order to perform one or more methods described herein, while other operations may be more general and/or specific to a particular programming language (e.g., C, C#, C++, Java, or other suitable programming languages, etc.).

The invention claimed is:

1. An augmented reality system for use in a medical procedure, comprising:
   a head mounted display comprising:
      a camera configured to detect light from a target;
      a near-eye display positioned between a wearer's eyes and the target, the near-eye display configured to display an image of the target based on the light detected by the camera, such that the image overlays a wearer's view of the target; and
      a distance sensor, configured to determine a distance between the head mounted display and the target throughout a medical procedure; and
   a processor, configured to:
      determine a mismatch between the image of the target obtained from the camera and the wearer's view of the target based on the value of the distance measured by the distance sensor, and a position of the wearer's eyes;
      adjust the position of the image on the near-eye display such that it is corrected based on the determined mismatch such that the image matches the wearer's view of the target; and
      repeat the determination of the mismatch and the adjustment of the position of the image throughout the medical procedure to take into account changes in the distance measured by the distance sensor throughout the medical procedure.

2. The system of claim 1, wherein the processor is further configured to determine the mismatch between the image of the target obtained from the camera and the wearer's view of the target by being configured to:
   assign a position in space to act as a fixed reference point;
   generate a 3D model of the target based on the light detected by the camera;
   determine the position and orientation of the target relative to the fixed reference point based on the distance measured by the distance sensor;
   determine the position of the wearer's eyes relative to the fixed reference point;
   determine the position and orientation of the head mounted display relative to the fixed reference point.

3. The system of claim 2, wherein the position and orientation of the head mounted display relative to the fixed reference point is the position and orientation of at least one of: the near-eye display, the distance sensor, and the camera.

4. The system of claim 2, wherein the processor is further configured to adjust the position of the image on the near-eye display such that it is corrected based on the determined mismatch by being configured to:
   set the position of the 3D model of the target relative to the fixed reference point;
   render the 3D model of the target to form the adjusted image based on the determined positions and orientations of the target, and head mounted display and the position of the wearer's eyes; and
   display the adjusted image on the near-eye display.

5. The system of claim 1, wherein the head mounted display further comprises an eye tracking sensor, the eye tracking sensor configured to continually determine the position of the wearer's eyes throughout the medical procedure, such that the repetition of the determination of the mismatch and the adjustment of the position of the image throughout the medical procedure takes into account changes in the position of the wearer's eyes throughout the medical procedure.

6. The system of claim 1, wherein the processor is further configured to determine the mismatch between the image of the target obtained from the camera and the wearer's view of the target by being configured to:
determine a disparity of the wearer's eyes from the determined distance and the position of the wearer's eyes.

7. The system of claim 1, wherein the distance sensor is a time of flight distance sensor, or a simultaneous localization and mapping (SLAM) sensor, or a visual SLAM (vSLAM) sensor.

8. The system according to claim 1, further comprising a light source, the light source configured to emit light such that it is incident on the target and subsequently detected at the camera.

9. The system according to claim 8, wherein the head mounted display comprises the light source.

10. The system of claim 1, wherein the light is near infra-red light.

11. The system according to claim 1, wherein the head mounted display comprises the processor.

12. The system according to claim 1, wherein the head mounted display comprises a plurality of cameras configured to detect the excited light.

13. The system according to claim 1, wherein the camera comprises the distance sensor.

14. A method of adjusting the position of an image in an augmented reality system for use in a medical procedure, the system comprising a head mounted display and a processor, the method comprising:
detecting light excited from a target;
determining a distance between the head mounted display and the target throughout a medical procedure;
displaying on a near-eye display positioned between a wearer's eyes and the target, an image of the target based on the detected light, such that the image overlays a wearer of the head mounted display's view of the target through the steps of:
determining a mismatch between the image of the target obtained from the camera and the wearer's view of the target based on the value of the determined distance, and a position of the wearer's eyes; and
adjusting the position of the image on the near-eye display such that it is corrected based on the determined mismatch.

15. A non-transitory computer readable medium, that when executed on a processor is configured to perform the steps of claim 14.

* * * * *